United States Patent [19]
Morrey et al.

[11] Patent Number: 5,704,909
[45] Date of Patent: Jan. 6, 1998

[54] BONE CLEANING AND DRYING SYSTEM

[75] Inventors: Bernard F. Morrey, Rochester, Minn.; John J. McLeod, Jr., Grand Forks, N. Dak.; Frederick M. Schultz, Rochester, Minn.

[73] Assignee: Mayo Foundation for Medical Education and Research

[21] Appl. No.: 650,342

[22] Filed: May 20, 1996

Related U.S. Application Data

[63] Continuation-in-part of Ser. No. 405,500, Mar. 16, 1995, Pat. No. 5,554,111.
[51] Int. Cl.$^6$ .................................................. A61N 1/30
[52] U.S. Cl. ........................... 604/26; 604/28; 604/35; 433/29
[58] Field of Search ........................... 604/21, 26, 28, 604/35, 118, 119; 433/80, 84, 85, 91, 29; 623/16–23

[56] References Cited

U.S. PATENT DOCUMENTS

| | | | |
|---|---|---|---|
| 4,380,435 | 4/1983 | Raeder et al. | 433/80 |
| 4,872,837 | 10/1989 | Issalene | 433/29 |
| 4,957,483 | 9/1990 | Gosner et al. | 604/30 |

OTHER PUBLICATIONS

Enhancing the Cement–Bone Interface with Pressurized CO2 Gas Drying, a presentation, made at the Leroy C. Abbott Orthopaedic Society meeting in San Fransisco meeting on May 3, 1996.

*Primary Examiner*—John D. Yasko
*Attorney, Agent, or Firm*—John T. Roberts

[57] ABSTRACT

A bone cleaning and drying system for cleaning drying and emptying bones during joint replacement surgery, which includes an applicator for applying compressed gas, namely carbon dioxide, to the intramedullary canal and the cancellous bone, with an applicator nozzle at the distal end, the applicator nozzle having a plurality of end discharge slits and a plurality of angled side discharge slits to provide reverse flow, which provides a pressure gradient from the distal end to the proximal end, which aspirates and directs the entrained air, blood, fluids, fat, marrow, tissue and bone debris onto a drape or a hollow deflector shield surrounding the applicator, the front surface of the hollow deflector shield being apertured to allow the entrained materials to pass therethrough, the interior of the hollow deflector shield being connected to a flexible suction hose, and replaces room air with carbon dioxide in bone.

9 Claims, 7 Drawing Sheets

FIG. 1
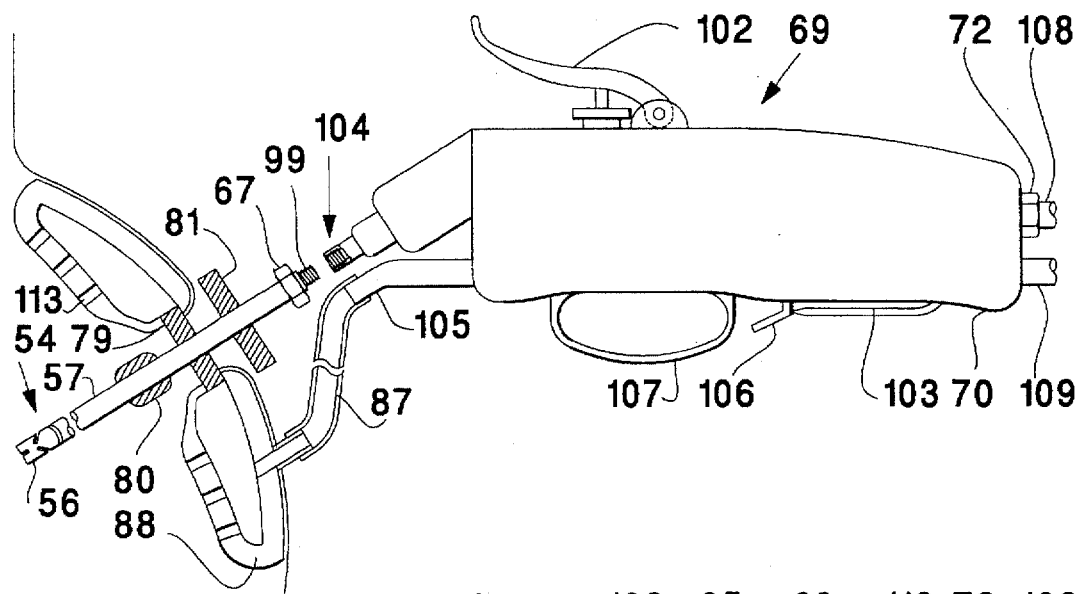
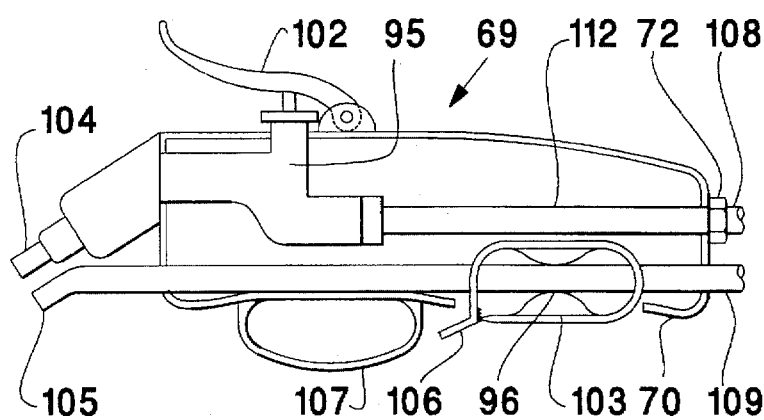
FIG. 2

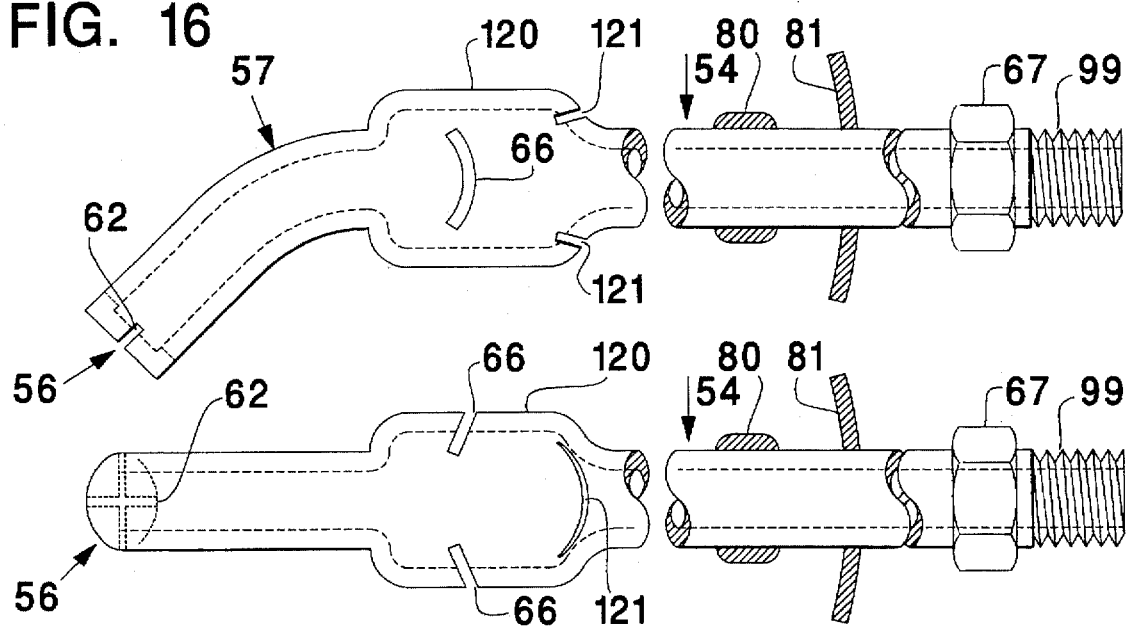
FIG. 16
FIG. 17
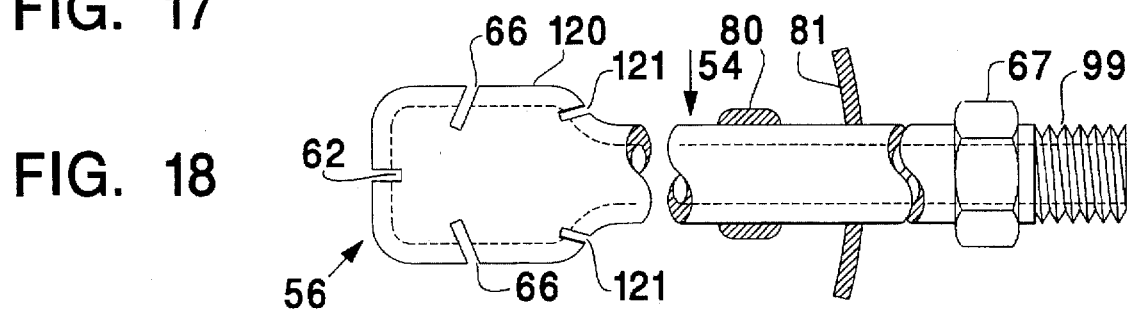
FIG. 18
FIG. 19

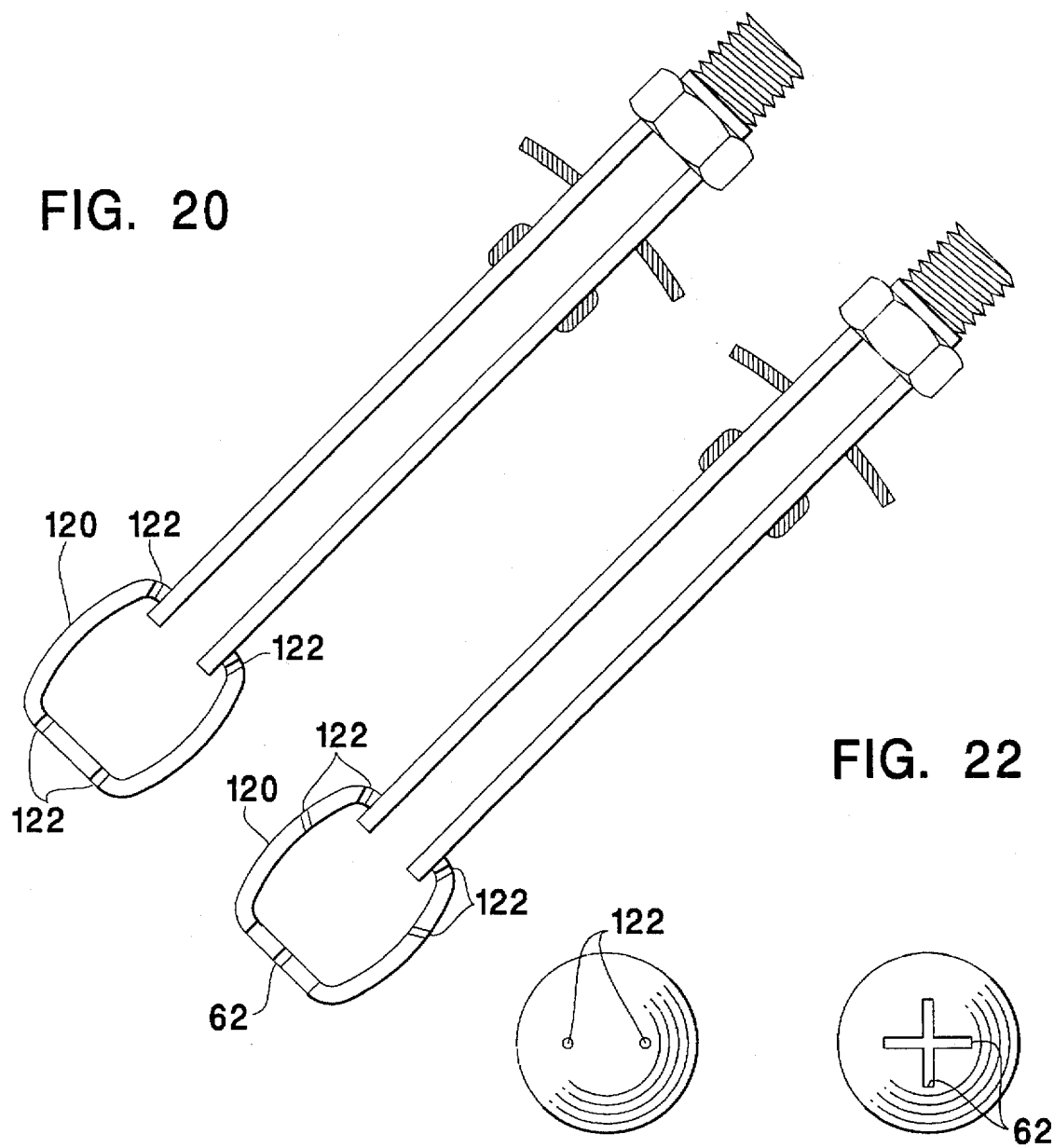

BONE CLEANING AND DRYING SYSTEM

CROSS-REFERENCE TO RELATED APPLICATION

This application is a continuation-in-part of our application entitled BONE CLEANING and DRYING SYSTEM, Ser. No. 08/405,500, filed on Mar. 16, 1995, now U.S. Pat. No. 5,554,111 the priority of which is claimed for the common subject matter.

BACKGROUND OF THE INVENTION

The practice of joint replacement surgery is now several decades old. The steps for this surgery involve exposing the cancellous bone, and in many locations, the intramedullary canal A properly shaped cavity must be created in the bone to accept the insertion of the prosthetic implant and any bone cement which may be inserted to secure the prosthetic implant in position.

In cases where an intramedullary canal is involved, a plug of bone, bone cement or plastic, a "intramedullary plug", is inserted into the intramedullary canal at the lowest level for the bone cement to fill and reach. Thereafter when the bone cement is inserted under pressure, and even more so when the prosthetic implant is inserted, the bone cement is forced into the intertrabecular spaces of the cancellous bone. This achieves mechanical interdigitation of cement and bone, thus maintaining the prosthetic implant in position and preventing it from becoming loose.

The air, blood, fluids, fat, marrow, tissue and bone debris in the intramedullary canal and the intertrabecular spaces of the adjacent cancellous bone must be removed from that area before the bone cement will be able to penetrate to the necessary depth, so that the bone cement is in direct contact with the bone without any interposed material.

The standard method of bone preparation today is surgical lavage, using an irrigating fluid such as sterile saline, followed by suction, to remove the air, blood, fluids, fat, marrow, tissue and bone debris, and then inserting gauze surgical sponge. This accomplishes only incomplete drying of the bone, and only incomplete removal of the air, blood, fluids, fat, marrow, tissue and bone debris, particularly in the small intertrabecular spaces of the cancellous bone in the femur adjacent the intramedullary canal. As a result the penetration depth of the bone cement is less than optimal, and the direct apposition of bone cement to bone is less than optimal, which results in a weaker, less secure fixation of bone cement in the bone. In addition the gauze surgical sponge may leave some cotton fibers in the opening, on the rough sharp edges of the bone, which can lead to osteolysis after the surgical procedure.

The amount of air, blood, fluids, fat, marrow, tissue and bone debris left in the cavity is decreased by inserting the bone cement through a cement gun which introduces the bone cement at the bottom of the cavity. The bone cement thus forces some of the air, blood, fluids, fat, marrow, tissue and bone debris up and out of the cavity as the bone cement is inserted, but also any of those materials remaining in the cavity or the bone may be forced back into the vascular channels as emboli.

The principal adverse complications of joint replacement surgery, listed below, may all be caused by the presence of unremoved significant amounts of one or more of air, blood, fluids, fat, marrow, tissue and bone debris.

Loosening of Bone Cement or Prosthetic Implant. This may occur if the bone surface, the underlying cancellous bone, or the intramedullary canal are not cleaned, dried, and emptied of air, blood, fluids, fat, marrow, tissue and bone debris. These materials may prevent the bone cement from penetrating and filling certain areas and fixation is not as secure as optimal. When fixation is not secure, micromotion may occur and gradually increase, resulting in more serious loosening and eventual failure of the operation.

Air Emboli (air forced into the blood stream). This may occur when room air is left in the intramedullary canal or in the intertrabecular spaces of the cancellous bone prior to the time the bone cement is forced into the intramedullary canal or cancellous bone. This air may be forced into the circulatory system when the bone cement and then the prosthetic implant is forced into the bone. While it is rare for large emboli to form, that is a very serious complication.

Embolization of other substances in the intramedullary canal such as blood, fluids, fat, marrow, tissue and bone debris. This occurs in a similar manner as air embolization, as described above. This also may be a very serious complication.

Contamination of the operating room and personnel with the patient's air, blood, fluids, fat, marrow, tissue and bone debris occur when the materials are blown out of the cavity and are not directed, confined and collected.

Nearly sixty years ago, a combination compressed air and suction instrument was disclosed for use in oral surgery, U.S. Pat. No. 1,987,907, granted Jan. 15, 1935, Combination Surgical Air Blast and Suction Tip, Joseph B. Jenkins. The use of carbon dioxide, as the compressed gas, in these instruments was disclosed in U.S. Pat. No. 2,812,765, granted Nov. 12, 1957, Combination Aspirator and Fluid-Delivering Surgical Instrument, Benjamin F. Tofflemire. The use of compressed air to dry a bone prior to attaching a dental implant is disclosed in U.S. Pat. No. 4,380,435, granted Apr. 19, 1983, Permanent One Visit Bonded Bridge No Drilling, and Kit Therefore, Arthur Raeder; Celia R. Raeder.

The use of carbon dioxide in joint replacement surgery to flush air out of the intramedullary canal and adjacent cancellous bone just prior to the insertion of bone cement was shown to eliminate clinically detectable air emboli in Prevention of Air Emboli in Hip Surgery, Harvey, P B and Smith, J A, *Anesthesia*, 1982, Vol. 37, pages 714–717. To prevent loosening of the prosthetic implant from occurring, all available methods should be used to clear the intertrabecular spaces of all air, blood, fluids, fat, marrow, tissue and bone debris, to a depth of 6 mm prior to introduction of the bone cement, Noble, P. C. & Swarts, E., Penetration of Acrylic Bone Cements into Cancellous Bone, *Acta. Orthop. Scand.* 54, 566–573, 1983.

U.S. Pat. No. 5,037,437, granted Aug. 6, 1991, filed Jan. 19, 1990, titled Method of Bone Preparation for Prosthetic Fixation, Frederick A. Matsen III, also discloses the use of carbon dioxide to "blow out" the air, blood, fluids, fat, marrow, tissue and bone debris from the intramedullary canal and to dry the cancellous bone. The configuration of the delivery nozzle is not disclosed and is stated to be not critical. Concurrently with the application of the carbon dioxide, suction to the bone may be employed to remove the debris and liquids dislodged by the compressed gas.

SUMMARY OF THE INVENTION

A bone cleaning and drying system for cleaning drying and emptying bones during joint replacement surgery, which includes an applicator for applying compressed gas, namely carbon dioxide, to the intramedullary canal and the cancellous bone, with an applicator nozzle at the distal end, the applicator nozzle having a plurality of end discharge slits and a plurality of angled side discharge slits to provide reverse flow, which provides a pressure gradient from the distal end to the proximal end, which aspirates and directs the entrained air, blood, fluids, fat, marrow, tissue and bone debris onto a drape or a hollow deflector shield surrounding the applicator, the front surface of the hollow deflector shield being apertured to allow the entrained materials to pass therethrough, the interior of the hollow deflector shield being connected to a flexible suction hose, and replaces room air with carbon dioxide in bone.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scope of the invention will be indicated in the claims.

BRIEF DESCRIPTION OF THE DRAWINGS

The invention will be better understood and the objects other than those set forth above will become apparent when consideration is given to the following detailed description thereof. Such description makes reference to the annexed drawings wherein:

FIG. 1 is a side view, partially in section, of the present invention;

FIG. 2 is an enlarged side view, partially in section, of the handpiece of FIG. 1;

FIG. 16 is a side view of an alternative embodiment of the present invention showing an angled applicator shaft with an enlargement of the cylinder near the angle of the applicator shaft;

FIG. 17 is a top view of the applicator of FIG. 16;

FIG. 18 is a side view of an alternative embodiment of FIG. 16 with a straight applicator shaft;

FIG. 19 is a end view of the applicator shaft of FIG. 16;

FIG. 20 is a side view, partially in section, of an alternative embodiment of the present invention showing an applicator shaft with an enlargement of the cylinder near the end of the applicator shaft and holes, not slits, in the shaft;

FIG. 21 is a end view of the applicator shaft of FIG. 20;

FIG. 22 is a side view, partially in section, of an alternative embodiment of the present invention showing an applicator shaft with an enlargement of the cylinder near the end of the applicator shaft and holes in the sides and proximal end of the enlargement of the shaft;

FIG. 23 is a end view of the applicator shaft of FIG. 22;

DESCRIPTION OF THE PREFERRED EMBODIMENTS

Figure 3:
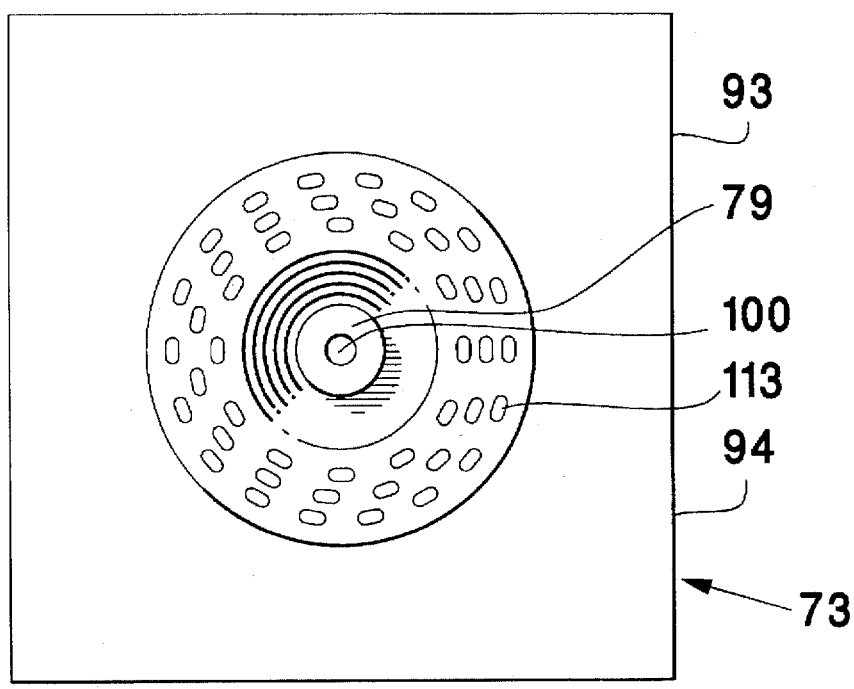
FIG. 3 is an enlarged front view of the hollow deflector shield of FIG. 1.

FIGS. 1, 2, 3, 7 and 8 disclose the preferred embodiment of the bone cleaning and drying system. The principal components are the applicator 54, the hollow deflector shield 88 and the handpiece 69.

Beginning at the distal end, there is an applicator 54, which comprises a applicator nozzle 56 attached to the distal end of an applicator shaft 57 which has an externally threaded proximal end 99. Surrounding the applicator shaft 57 is an oval shaped shaft ridge 80, a cylindrical shaft disk 81 and a hexagonal shaped coupling hub 67. The proximal end 99 of the applicator shaft 57 is externally threaded.

Also surrounding the applicator shaft 57 is a hollow deflector shield 88 having a suction port facing to the rear around which one end of flexible suction hose 87 of the handpiece 69 fits. The hollow deflector shield 88 has a plurality of oval shaped apertures 113 in the front surface. Both the front wall and the back wall of the hollow deflector shield 88 are made of clear plastic. The inner end of the front and back walls of the hollow deflector shield 88 attach to the outer edges of a resilient washer 79 which has a central aperture 100. The applicator shaft 57 fits snugly through, and in sliding engagement with, the resilient washer 79. The resilient washer 79 is slid from the distal end of the applicator 54 over the shaft ridge 80, against the shaft disk 81. Around the hollow deflector shield 88 is a drape 73 of absorbent material cloth, paper, or synthetic product.

Detachably connected to the proximal end 99 of the applicator shaft 57 is the internally threaded stub end 104 of the handpiece 69. At the other end of the handpiece 69 is a gas supply coupling 72 connected to a gas supply hose 108, which is connected to a gas supply source, such as a hospital central supply. The compressed gas is carbon dioxide which, because of its high diffusion coefficient, dissolves rapidly in the vascular system and prevents air embolization, and also dries the bone.

The handpiece 69 has a hand grip 70 and finger support ring 107 which the surgeon grasps to control the handpiece 69. The handpiece 69 has a rigid gas pipe 112 between the gas supply coupling 72 and a gas control valve 95. The gas control valve 95 is controlled by a thumb gas release lever 102. The gas control valve 95 is also connected to the internally threaded stub end 104.

Also detachably connected to the suction port of the hollow deflector shield 88 is the flexible suction hose 87 of the handpiece 69. The flexible suction hose 87 is also connected to a semi-rigid suction tube 109, which runs through the handpiece 69 and is connected to a vacuum source, such as the central supply. The handpiece 69 has a suction control clamp 96, controlled by suction turn on control 106, and suction shut off control 103, which open or close the semi-rigid suction tube 109 and control the suction to flexible suction hose 87.

The construction of the suction turn on control 106 and the suction shut off control 103 are similar to a conventional clamp used on surgical irrigation systems, where the flow can be opened or closed with one hand. Here the fifth finger depresses the suction shut off control 103 to close the suction control clamp 96, and the forward edge of the suction shut off control 103 catches on detentes in the suction turn on control 106, which is biased against the suction shut off control 103. The suction control clamp 96 is opened by the surgeon depressing suction turn on control 106 with his ring finger, thus rotating the suction turn on control 106 slightly forward, releasing suction shut off control 103.

Figure 7:
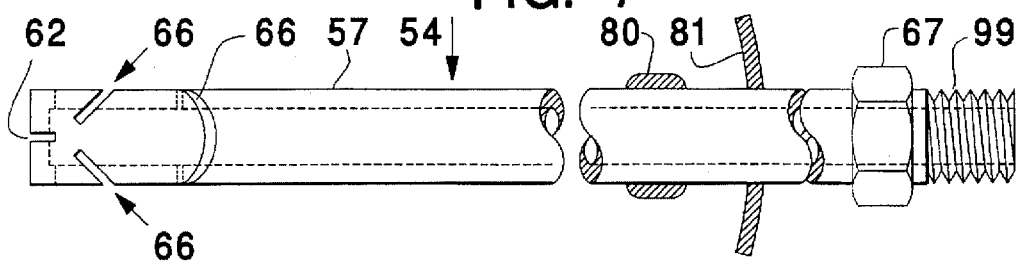
FIG. 7 is a side view of the applicator with end discharge slits and angled reverse flow slits.
Figure 8:
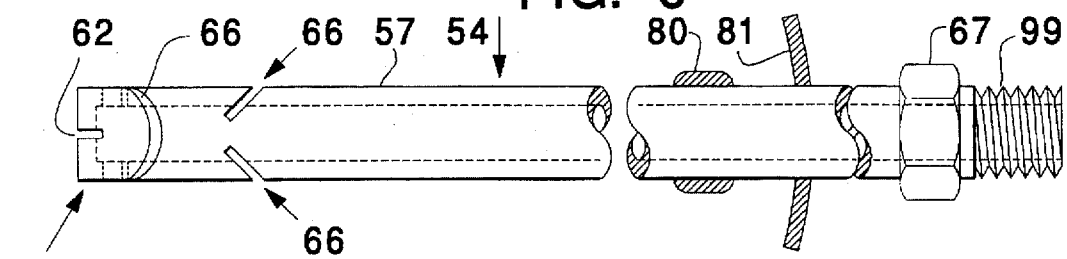
FIG. 8 is a top view of the applicator of FIG. 7.

FIGS. 7 and 8 disclose the applicator shaft 57 of FIG. 1 with two pair of reverse flow side discharge slits 66 and a pair of end discharge slits 62. The side discharge slits 66 are angled at 45° to the axis of the applicator shaft 57. The slits are 0.25 mm wide, the end discharge slits 62 are 1.2 mm deep, and the side discharge slits 66 are 2.4 mm deep.

The outside diameter of the applicator shaft 57 is 4.8 mm and the inside diameter is 3.7 mm. The length and diameter of the applicator shaft 57 of the applicator 54 is dependant on the application. For a femoral canal the length will be 200–350 mm.

Alternate Embodiments

Figure 4:
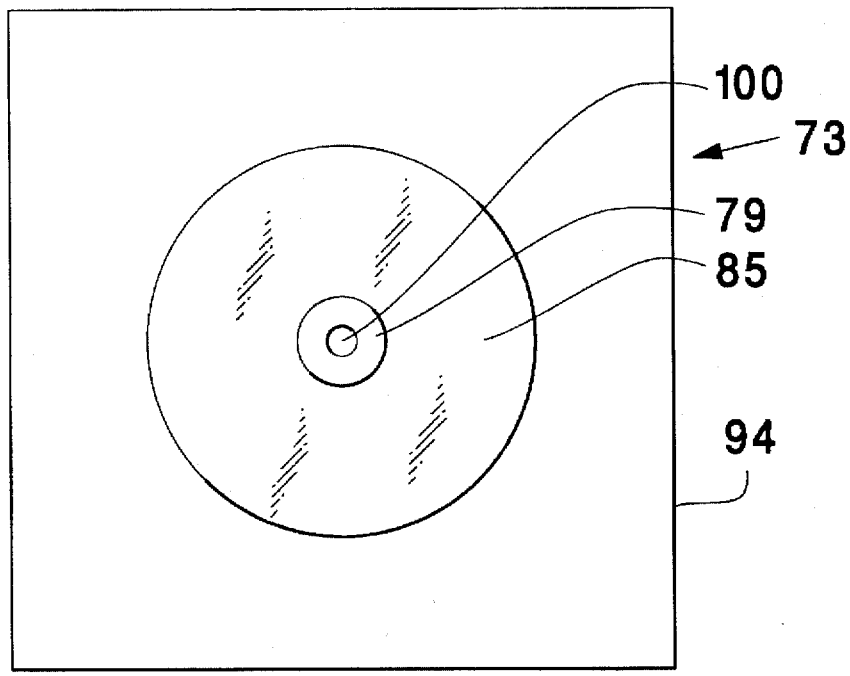
FIG. 4 is a front view of an alternative embodiment of the present invention, disclosing a two part drape with the central section a rigid deflector shield.
Figure 5:
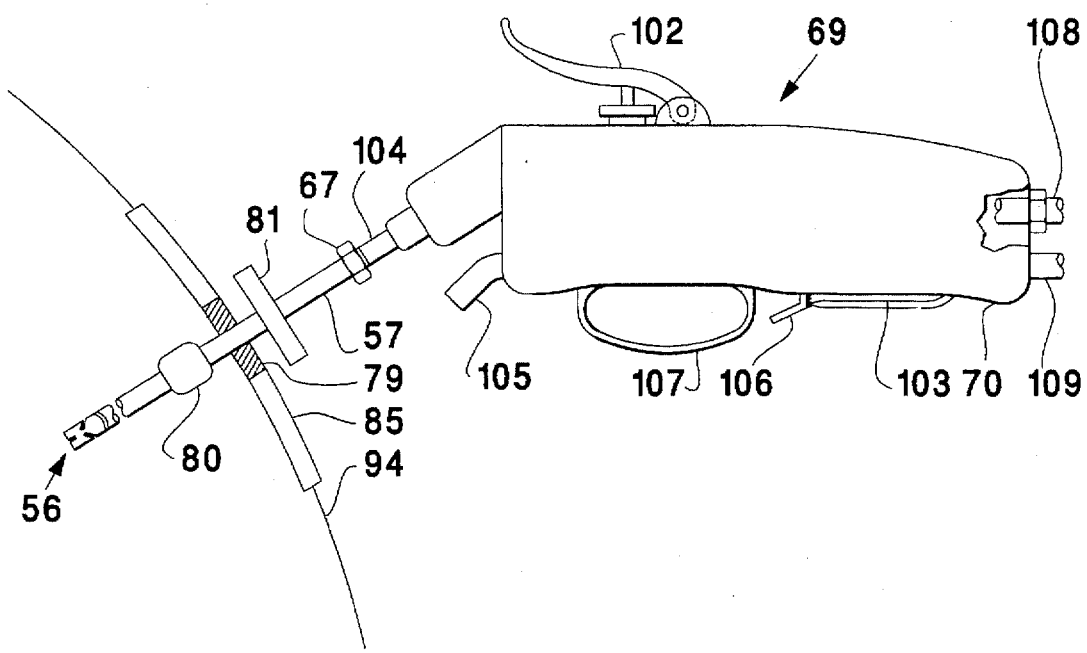
FIG. 5 is a side view of the drape of FIG. 4.

FIGS. 4 and 5 disclose an alternative embodiment of the present invention with a plain drape 73. The drape 73 may be square, rectangular, oval or other geometric shape. There is a central aperture 100 formed by a resilient washer 79, through which the applicator shaft 57 of the applicator 54 fits. Behind the central aperture 100 is a shaft disk 81, and in front of it is a shaft ridge 80, over which the drape 73 is slid.

Surrounding the central aperture 100 is the central section 85, and surrounding the central section 85 is the peripheral section 94. The central section 85 may be of opaque absorbent material of cloth, paper, or synthetic product or may be of clear plastic. The peripheral section 94 may be of clear plastic. Alternatively the drape 73 may be made entirely of opaque absorbent material or entirely of clear plastic. An alternative to the resilient washer 79 is a button hole, through which the applicator shaft 57 of the applicator 54 passes.

Figure 6:
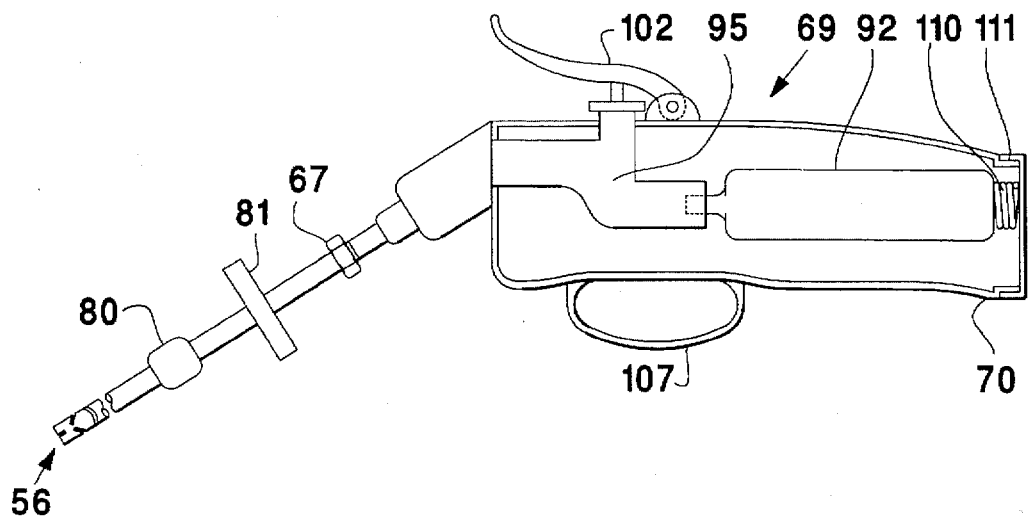
FIG. 6 is a side view, partially in section, of an alternative embodiment of the present invention with a pressurized cartridge gas supply source.

FIG. 6 discloses an alternative embodiment of the present invention in which the compressed gas is supplied by one or more conventional pressurized cartridge 92, instead of using the hospital central supply. The pressurized cartridge 92 is biased against the gas control valve 95 by cartridge spring 110, which presses against cartridge screw cap 111. In this embodiment, the handpiece 69 is unconnected to any central supply, and therefore there is neither a flexible suction hose 87, a suction turn on control 106, nor a suction shut off control 103. The drape 73 of FIG. 4 is thus used instead of the hollow deflector shield 88. Where suction, but not carbon dioxide, is available from the central supply, the applicator can include a hollow deflector shield 88 connected to a flexible suction hose 87.

Alternatively, the compressed gas may be supplied by a portable tank, instead of pressurized cartridge 92. The portable tank would be attached to the handpiece 69 of FIG. 1.

Figure 9:
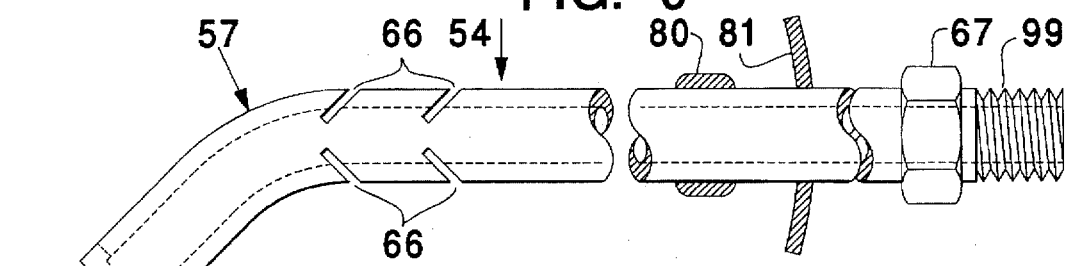
FIG. 9 is a side view of an alternative embodiment of the present invention showing an angled applicator shaft of the applicator.
Figure 10:
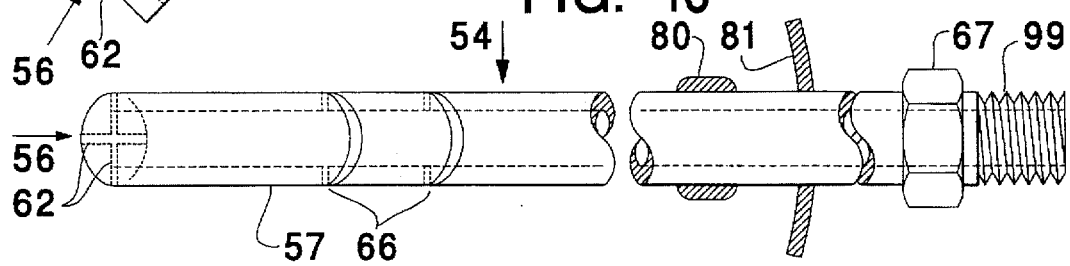
FIG. 10 is a top view of the applicator of FIG. 9.
Figure 11:
FIG. 11 is a end view of the applicator shaft of FIG. 9.

FIGS. 9 to 11 disclose an alternative embodiment of the present invention where the applicator shaft 57 is angled near the distal end. The applicator nozzle 56 has a pair of end discharge slits 62 and two pairs of side discharge slits 66 angled at 45° to the axis of the applicator shaft 57.

Figure 12:
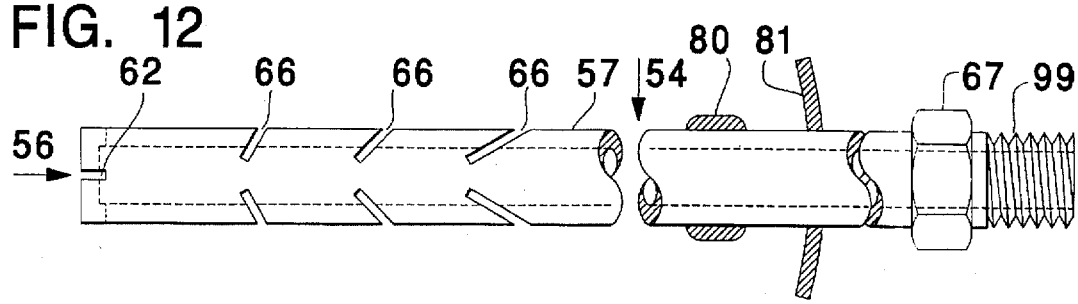
FIG. 12 is an alternative embodiment of the present invention disclosing a side view of the applicator with 3-angled reverse flow side discharge slits, each pair having a different angle.
Figure 13:
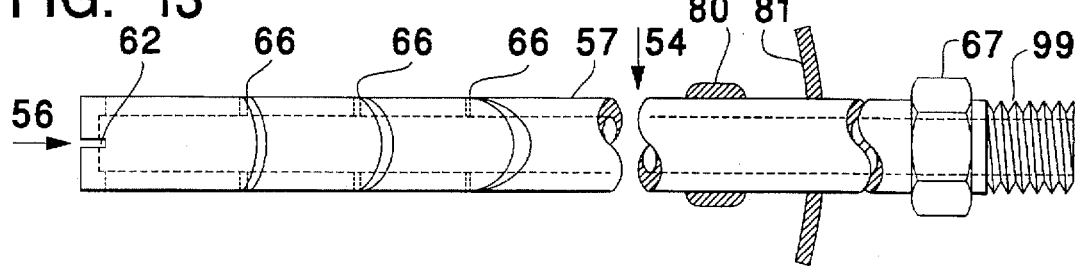
FIG. 13 is a top view of the applicator of FIG. 12.

FIG. 12 and 13 discloses three pairs of reverse flow side discharge slits 66. These are each differently angled, being at 25°, 45° and 60°, to the axis of the applicator shaft 57, from the distal toward the proximal end. The applicator nozzle 56 has a pair of end discharge slits 62 at the distal end of the applicator shaft 57.

Figure 14:
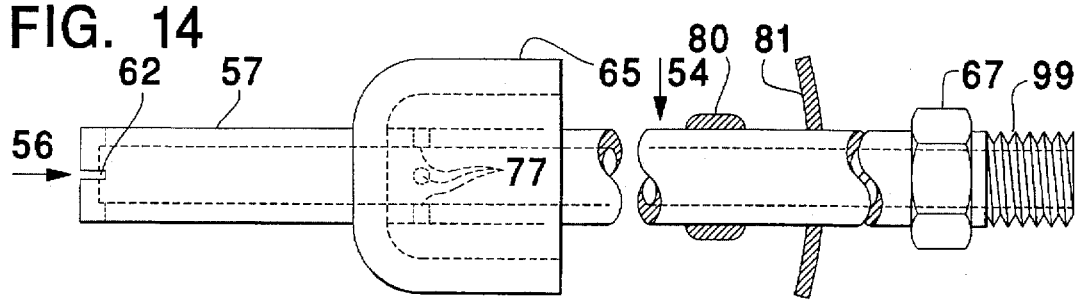
FIG. 14 is a side view of the applicator of an alternative embodiment of the present invention with a shaft cup; and, FIG. 15 is an alternative embodiment of the present invention with a shaft cup and a angled applicator shaft.
Figure 15:
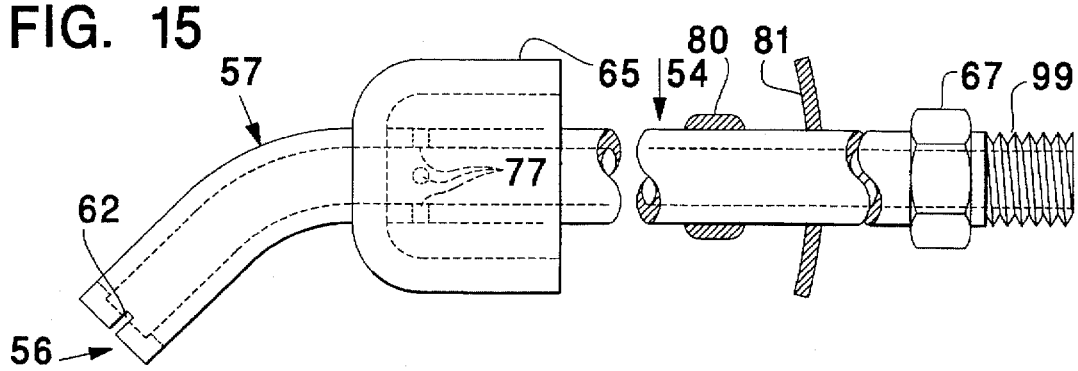

FIGS. 14 and 15 disclose two versions of an alternative embodiment of the present invention. Each has a shaft cup 65. Inside the shaft cup 65 are four small holes 77 around the periphery of the applicator shaft 57, in addition to the end discharge slits 62 at the distal end of the applicator shaft 57. This causes a reversed flow direction to the compressed gas exiting the small holes 77.

The applicator shaft 57 disclosed in FIG. 15 is angled below the shaft cup 65 and near the distal end at 70° to permit it to be used in the acetabulum, shoulder and whichever other locations this configuration is more effective or convenient for accessibility to the area to be treated.

FIGS. 16 to 23 disclose alternative embodiments of the present invention where the applicator shaft 57 has an enlargement near or at the distal end, for the purpose of permitting a more powerful reverse flow, as will be explained below.

FIGS. 16, 17 and 19 disclose an alternative embodiment of FIGS. 9 and 10 where the applicator shaft 57 is angled near the distal end. Above the distal end is an cylindrical enlargement 120 of the shaft. Where the proximal end of the enlargement bulges outward from the shaft are two slits 121 on the opposite sides of the enlargement, nearly parallel to the axis of the shaft. The slits are through the wall of the enlargement. The applicator nozzle 56 has a pair of end discharge slits 62 and two pairs of side discharge slits 66 angled at about 45° to the axis of the applicator shaft 57.

FIGS. 18 discloses an alternative embodiment of FIG. 7 where the applicator shaft 57 is straight, not angled. At the distal end is an cylindrical enlargement 120 of the shaft. Where the proximal end of the enlargement bulges outward from the shaft are two slits 121 on the opposite sides of the enlargement, nearly parallel to the axis of the shaft. The slits are through the wall of the enlargement. The applicator nozzle 56 has a pair of end discharge slits 62 and two pairs of side discharge slits 66 angled at about 45° to the axis of the applicator shaft 57.

FIGS. 20 to 23 disclose alternative embodiments of FIG. 18 where the applicator shaft 57 distal end is an cylindrical enlargement 120 of the shaft, made from a separate piece of metal or plastic, incorporated near the end of the shaft. In both, there are a series of holes 122 around the proximal end of the enlargement 120. In FIG. 20, the distal end of enlargement 120 has two holes 122. In FIG. 22, the distal end of enlargement 120 has a pair of end discharge slits 62.

By way of example, in FIGS. 20 to 23, the outer diameter of the enlargements 120 may be 6 mm, the wall thickness of the enlargements may be 2 mm., and the diameter of the holes 122 may be 1 mm. There may be six or more evenly spaced holes 122 around the proximal end of the enlargement 120.

Operation of Disclosed Embodiments

The operation of the embodiment disclosed in FIGS. 1–3, 7 and 8 will be described initially. Prior to the operation the surgeon selects the proper applicator shaft 57, with the applicator nozzle 56 attached. As described previously, the hollow deflector shield 88 is slid up the applicator shaft 57 from the applicator nozzle 56, and seated between the shaft ridge 80 and the disk 81. The externally proximal end 99 of the applicator shaft 57 is screwed into the internally threaded stub end 104 by rotating coupling hub 67. The flexible suction hose 87 is attached to the rear facing tube of the hollow deflector shield 88 and to forward end 105 of the semi-rigid suction tube 109. The gas supply hose 108 is attached to the handpiece 69 by rotating gas supply coupling 72. The semi-rigid suction tube 109 is attached to the vacuum source, and the suction shut off control 103 is depressed, closing the suction control clamp 96.

The applicator 54 disclosed here is especially designed for cleaning the intramedullary canal of bones such as the femur, after the bone has been mechanically shaped to accept the prosthetic implant and the intramedullary plug has been inserted.

The surgeon inserts the applicator 54 into the intramedullary canal after the surgical lavage has been completed. The applicator nozzle 56 reaches to the bottom of the cavity before the surgeon releases the compressed gas into the applicator 54. The surgeon presses the suction turn on control 106 just before pressing the thumb gas release lever 102, thus opening both the suction control clamp 96 with the gas control valve 95. The compressed gas exits the end discharge slits 62 both distally and laterally. The compressed gas exits the side discharge slits 66 in a reversed flow direction. The majority of the air, blood, fluids, fat, marrow, tissue and bone debris is entrained through the multiple apertures 113 and into the vacuum source. The remainder of the material goes onto the peripheral section 94 of drape 73.

This reverse flow of the compressed gas creates a strong negative pressure distal the level of the reverse flow side discharge slits 66 and for the length of the intramedullary canal along the reverse flow side discharge slits 66. As the blood, fluids, fat, marrow, tissue and bone debris are loosened by the jets of carbon dioxide exiting the end discharge slits 62 and the reverse flow side discharge slits 66, those substances are aspirated into the stream of carbon dioxide moving at a high velocity and low pressure, and carried out of the cavity in a narrow focused cone, and onto the distal surface of the hollow deflector shield 88.

In treating the intramedullary canal, the applicator nozzle 56 is inserted to the intramedullary plug and then is pulled back slowly in a spiral motion to keep the applicator nozzle 56 near all of the exposed surface of the cancellous bone in sequence. The procedure usually needs to be repeated several times in succession. This procedure cleans, drys, and empties the cavity, surface and the underlying bone, including the intertrabecular spaces of the adjacent cancellous bone to allow the bone cement to penetrate to a greater depth, and complete direct apposition of bone cement and bone. This results in a stronger bone-cement interface, and makes it less likely that air, blood, fluids, fat, marrow, tissue and bone debris will be forced into the vascular system causing embolization. After the exposed intramedullary canal and cancellous bone have been cleaned dried and emptied, while the bone is still largely filled with carbon dioxide, the bone cement is inserted promptly, with a known cement gun, followed by the prosthetic implant.

The applicator 54 shown in FIGS. 9, 10, 11 and 15 is designed for the more exposed areas and those with less deep intramedullary canals, drill holes, cavities, and areas of exposed and semi-exposed underlying cancellous bone such as the hip, knee, shoulder, elbow, wrist, and hand joints. The applicator shaft 57 is shorter and the applicator nozzle 56 has a pair of end discharge slits 62 as well as two pair of side discharge slits 66. The applicator 54 is inserted fully into the area and the compressed gas from the end discharge slits 62 and reverse flow side discharge slits 66 dries all cavities, the entire surface and underlying areas of the cancellous bone.

In the applicator 54 disclosed in FIG. 12, the lowest pair of side discharge slits 66 in the applicator nozzle 56 discharge the compressed gas nearly laterally to the cancellous bone to mechanically dislodge any air, blood, fluids, fat, marrow, tissue and bone debris. The intermediate and the upper pair of slits are more angled, forcing the compressed gas in a more proximal reversed flow direction.

The procedure in using the applicator 54 disclosed in FIG. 14 and 15 is essentially the same as described above. The applicator shaft 57 has two pair of small holes 77 spaced proximal from the base of, and within the shaft cup 65. The compressed gas exits the small holes 77 laterally, but is immediately turned into a reverse flow by the shaft cup 65.

The procedure in using the applicator 54 disclosed in FIGS. 16 to 23 is essentially the same as described above. In FIGS. 16 to 19, the central portions of the two slits 121 at the proximal end of the enlargement provide the major portion of the gas discharge in the reverse flow direction. The end portions of these slits 121 provide some lateral flow, as do the side slits 66. The end slits 62 and holes 122 provide gas flow to the bottom of the cavity to clean the bottom as well as the sides of the cavity. In FIGS. 20 to 23, the holes 122 provide gas flow to the bottom of the cavity to clean the bottom of the cavity.

It will thus be seen that the objects set forth above, among those made apparent from the preceding description, are efficiently attained and, since certain changes may be made in carrying out the above method and in the article set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A bone cleaning and drying system for use during joint replacement surgery and other types of surgery to remove and collect the air, blood, fluids, fat, marrow, tissue and bone debris from the cavities of the bone, comprising in combination:
   a) a handpiece having a gas control valve, and a gas supply hose connected to a gas supply source of a compressed gas;
   b) said gas control valve connected to an applicator for carrying the compressed gas to the cavity of the bone;
   c) said applicator having a applicator shaft whose proximal end is connected to the handpiece and whose distal end terminates in a applicator nozzle;
   d) said applicator nozzle having an cylindrical enlargement near its distal end, the proximal end of the enlargement having apertures which direct compressed gas in a reversed flow direction;

WHEREBY the cavity of the bone and the openings in the surrounding cancellous bone are cleaned emptied and dried during the surgery, and air, blood, fluids, fat, marrow, tissue and bone debris from the cavities of the bone are entrained for removal, prior to the insertion of the bone cement and the prosthetic implant.

2. The combination of claim 1 wherein said proximal end of the enlargement of said applicator nozzle has apertures which direct the majority of the compressed gas in a reversed flow direction.

3. The combination of claim 1 including a drape, said drape having a central section of absorbent material, and a peripheral section of clear plastic.

4. The combination of claim 1 wherein said handpiece has a suction control valve, and means to attach the suction control valve to a vacuum source.

5. The combination of claim 1 wherein the distal end of the applicator shaft has a aperture for the exiting of the compressed gas in a direction distal and lateral of the applicator shaft.

6. The combination of claim 3 wherein the gas supply source is a pressurized cartridge.

7. The combination of claim 4 wherein a hollow deflector shield surrounds the proximal end of the applicator shaft, onto which the entrained material from the cavities of the bone are directed when the applicator nozzle is inserted into said cavities, and compressed gas is discharged through the slit, the interior of the hollow deflector shield connected through a flexible suction hose to said suction control valve and to a vacuum source.

8. A bone cleaning and drying system for use during joint replacement surgery and other types of surgery to remove and collect the air, blood, fluids, fat, marrow, tissue and bone debris from the cavities of the bone, comprising in combination:

a) a handpiece having a gas control valve, and a gas supply hose connected to to a gas supply source of a compressed gas;

b) said gas control valve connected to an applicator for carrying the compressed gas to the cavity of the bone;

c) said applicator having a applicator shaft whose proximal end is connected to the handpiece and whose distal end terminates in a applicator nozzle;

d) said applicator nozzle having a slit on the side of the applicator shaft, said slit angled to the axis of the applicator shaft, to direct the compressed gas exiting the slit of the applicator nozzle in a reversed flow direction;

WHEREBY the cavity of the bone and the openings in the surrounding cancellous bone are cleaned emptied and dried during the surgery, and air, blood, fluids, fat, marrow, tissue and bone debris from the cavities of the bone are removed, prior to the insertion of the bone cement and the prosthetic implant.

9. The combination of claim 8 wherein the gas supply source is a pressurized cartridge.

* * * * *